(12) United States Patent
Bergman et al.

(10) Patent No.: US 8,842,273 B2
(45) Date of Patent: Sep. 23, 2014

(54) OPTICAL MEASUREMENT OF DRILLED HOLES

(71) Applicant: United Sciences LLC, Atlanta, GA (US)

(72) Inventors: Harris Bergman, Atlanta, GA (US); Henrik Iskov Christensen, Atlanta, GA (US); Karol Hatzilias, Atlanta, GA (US)

(73) Assignee: United Sciences, LLC, Atlanta, GA (US)

( * ) Notice: Subject to any disclaimer, the term of this patent is extended or adjusted under 35 U.S.C. 154(b) by 0 days.

(21) Appl. No.: 13/767,017

(22) Filed: Feb. 14, 2013

(65) Prior Publication Data

US 2014/0226156 A1   Aug. 14, 2014

(51) Int. Cl.
*G01N 21/00* (2006.01)
*G01N 21/954* (2006.01)

(52) U.S. Cl.
CPC .................................... *G01N 21/954* (2013.01)
USPC ................... 356/241.1; 356/241.5; 356/241.6

(58) Field of Classification Search
CPC ..................................................... G01N 21/954
USPC ........................................... 356/241.1–241.5
See application file for complete search history.

(56) References Cited

U.S. PATENT DOCUMENTS

| | | | |
|---|---|---|---|
| 4,561,776 A * | 12/1985 | Pryor | ................................ 356/72 |
| 4,839,526 A * | 6/1989 | Pryor | .......................... 250/559.4 |
| 4,967,092 A | 10/1990 | Fraignier et al. | |
| 5,254,859 A | 10/1993 | Carman et al. | |
| 5,557,438 A | 9/1996 | Schwartz et al. | |
| 5,804,830 A | 9/1998 | Shafir | |
| 5,859,364 A | 1/1999 | Toda et al. | |
| 6,181,411 B1 | 1/2001 | Harris et al. | |
| 6,758,564 B2 | 7/2004 | Ferguson | |
| 7,009,717 B2 | 3/2006 | Van Coppenolle et al. | |
| 7,016,052 B2 | 3/2006 | Bloch et al. | |
| 7,027,145 B2 * | 4/2006 | Segall et al. | ................ 356/241.1 |
| 7,251,366 B1 | 7/2007 | Silver et al. | |
| 7,329,860 B2 | 2/2008 | Feng et al. | |
| 7,428,061 B2 | 9/2008 | Coppenolle et al. | |
| 7,534,995 B2 | 5/2009 | Peters et al. | |
| 7,903,245 B2 | 3/2011 | Miousset et al. | |
| 8,035,823 B2 | 10/2011 | Keightley et al. | |
| 8,467,071 B2 | 6/2013 | Steffey et al. | |
| 2003/0106378 A1 | 6/2003 | Giannakopoulos et al. | |
| 2007/0070340 A1 * | 3/2007 | Karpen | ....................... 356/241.1 |
| 2007/0229806 A1 | 10/2007 | Lally et al. | |
| 2007/0247639 A1 | 10/2007 | Amstel et al. | |
| 2007/0296964 A1 * | 12/2007 | Nishimura et al. | ......... 356/241.1 |
| 2008/0062434 A1 | 3/2008 | Diefenbacher | |
| 2008/0106722 A1 | 5/2008 | Shibazaki | |

(Continued)

OTHER PUBLICATIONS

Devlieg et al., "Applied Accurate Robotic Drilling for Aircraft Fuselage", Technical paper, SAE 2010 Aerospace Manufacturing and Automated Fastening Conference & Exhibition, Sep. 2010, 8 pages, Society of Automotive Engineers (SAE) International, USA.

(Continued)

*Primary Examiner* — Michael P Stafira
(74) *Attorney, Agent, or Firm* — John R. Biggers; Biggers Kennedy Lenart Spraggins LLP (57) ABSTRACT

An apparatus is provided that includes an optical probe; and a robotic transport so adapted to the optical probe as to move the optical probe inside a drilled hole to measure the drilled hole at one or more depths.

17 Claims, 6 Drawing Sheets

(56) References Cited

U.S. PATENT DOCUMENTS

| | | |
|---|---|---|
| 2008/0156619 A1 | 7/2008 | Patel et al. |
| 2008/0283738 A1 | 11/2008 | Peters et al. |
| 2009/0208143 A1 | 8/2009 | Yoon et al. |
| 2010/0060904 A1 | 3/2010 | Keightley et al. |
| 2011/0211869 A1 | 9/2011 | Shouji et al. |
| 2011/0313558 A1 | 12/2011 | Lehman et al. |
| 2012/0184842 A1 | 7/2012 | Boularot et al. |
| 2012/0190921 A1 | 7/2012 | Yadlowsky et al. |
| 2012/0288336 A1 | 11/2012 | Berg |
| 2013/0158393 A1 | 6/2013 | Papac et al. |
| 2013/0218528 A1 | 8/2013 | Lind et al. |
| 2013/0237754 A1 | 9/2013 | Berglund et al. |

OTHER PUBLICATIONS

PCT Search Report and Written Opinion, May 28, 2014, PCT Application No. PCTUS2014015665, 13 pages.

PCT Search Report and Written Opinion, May 28, 2014, PCT Application No. PCTUS2014015670, 12 pages.

PCT Search Report and Written Opinion, May 19, 2014, PCT Application No. PCTUS2014015674, 28 pages.

PCT Search Report and Written Opinion, May 23, 2014, PCT Application No. PCTUS2014015676, 18 pages.

Notice of Allowance U.S. Appl. No. 14/099,482, Aug. 29, 2014 pp. 1-12.

\* cited by examiner

OPTICAL MEASUREMENT OF DRILLED HOLES

BACKGROUND

Much manufacturing today, particularly aerospace manufacturing, particularly during manufacture of commercial aircraft, hundreds of thousands of precisely located, straight holes are drilled, drilled by robotic systems that include drilling end effectors. After a group of holes has been drilled, the drilled holes are inspected to ensure that they are within tolerance. The inspection involves checking the diameter and circularity of each hole at different depths to ensure that each hole is straight and not elliptical, not conical, not hourglass-shaped. Such inspections are performed by human quality assurance inspectors, who inspect large groups of holes at one time, extremely laboriously. When a drill bit becomes chipped, its current hole and all its potentially thousands of subsequent holes are out of tolerance, none of which are identified inspection.

Prior art attempts to measure drill holes include focal microscopy for fringe pattern analysis, that is image analysis, by comparison with a pre-image of a correct hole, difficult to deploy and not very accurate. Other prior art include capacitive probes such as described for example in U.S. 2012/0288336. Such capacitive probes, however, take measurements in only one direction at a time, requiring multiple measurements to assess a hole, never assembling a complete image of the inside of a drilled hole. Moreover, a capacitive probe must fit tightly into a drilled hole, aligned closely to the center axis of the hole, and for calibration purposes, must have the same probe-to-hole-side separation at all times—because its capacitance is calibrated according to the thickness of the layer of air between the probe and the wall of the hole. When such a capacitive probe identifies a bad hole, and the hole is redrilled to a larger diameter, the capacitive probe must be swapped out to a larger diameter probe in order to remeasure the redrilled hole.

DETAILED DESCRIPTION OF EXAMPLE EMBODIMENTS

Figure 1:
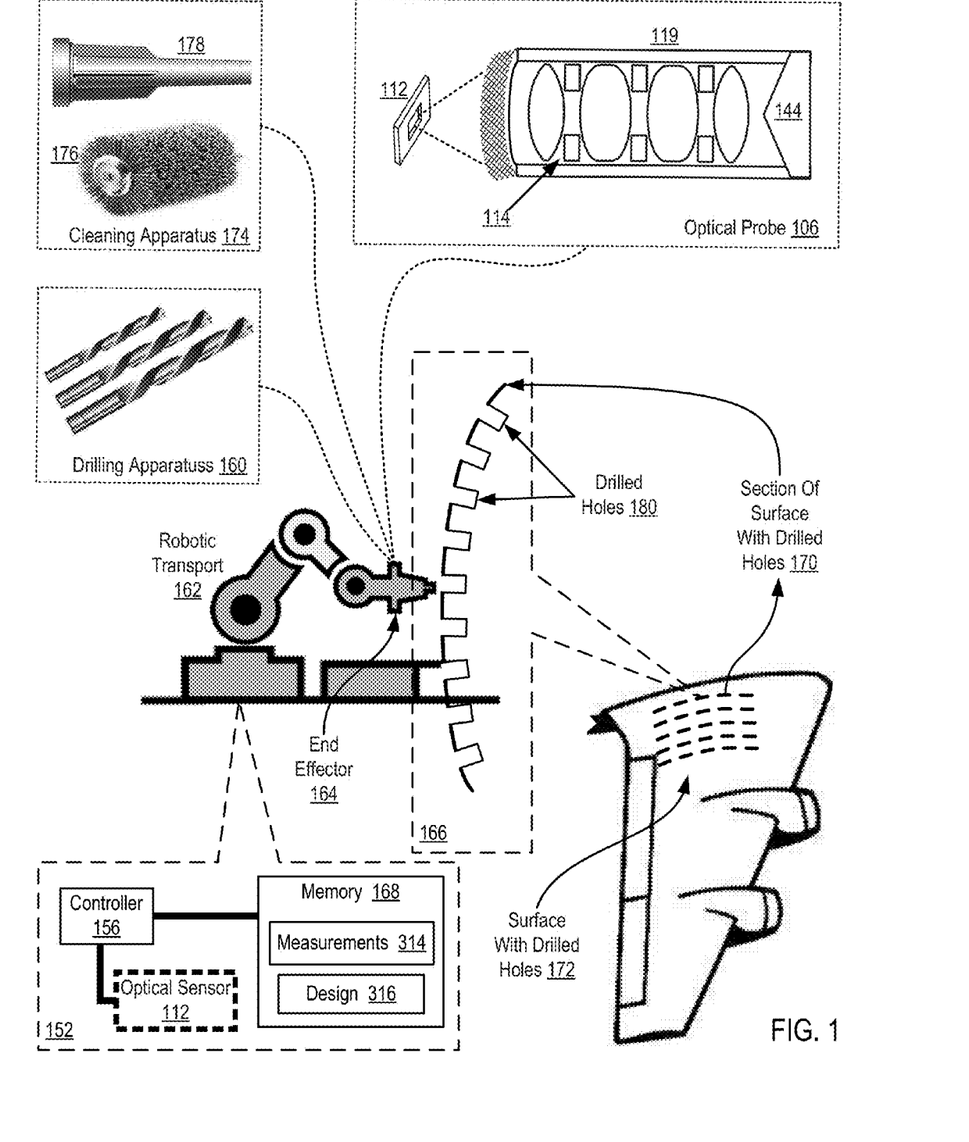
FIG. 1 sets forth a line drawing of example apparatus for optical measurement of drilled holes.

Example apparatus and methods for optical measurement of drilled holes according to embodiments of the present invention are described with reference to the accompanying drawings, beginning with FIG. 1. FIG. 1 sets forth a line drawing of example apparatus for optical measurement of drilled holes. The apparatus of FIG. 1 includes an optical probe (106) and a robotic transport (162). The robotic transport (162) is adapted to the optical probe (106) so as to move the optical probe inside a drilled hole (180) to measure the drilled hole at different depths.

In this example, the robotic transport is adapted to the optical probe by mounting the optical probe on an end effector (164) of the robotic transport. The optical probe may be mounted in a fixed position on the end effector, with drilling apparatus (160) also mounted in a fixed position on the end effector so that positioning the optical probe at a drilled hole after drilling requires reposition the robotic transport. Alternatively both drilling apparatus (160) and the probe (106) may be rotatably mounted on the end effector (164) with separate home positions and the same deployed position, so that, after drilling, the drilling apparatus (160) is rotated to its home position and the probe (106) is rotated into its deployed position to measure a drilled hole (180). As a further alternative, the optical probe (106) may be the only operable device on the end effector (164), so that a drilling apparatus (160) is mounted on an entirely separate transport, and the optical probe (106) follows along and measures a hole after the drill has drilled the hole and moved to a next location to drill a next hole.

In the example of FIG. 1, the optical probe projects as the optical probe rings of light on the inside of a drilled hole (180), and an optical sensor (112) receives through an optical lens (114) reflections of the projected rings. A controller (156) determines from the received reflections measurements (314) of the drilled hole (180). The controller determines by comparison of design measurements (316) and the measurements (314) of the drilled hole (180) whether the hole as drilled is within design tolerance. The measurements so compared typically include hole diameter and hole circularity. The controller (156) also in an embodiment infers from disparities among pixel values in the measurements (314) whether a crack may be present in a wall of a drilled hole (180).

In the example of FIG. 1, the controller (156) also determines, by comparison of design measurements (316) and the measurements (314) of the drilled hole, whether the hole as drilled fails to meet design tolerance. If a hole so fails, the controller is configured to instruct the drilling apparatus (160) to redrill the hole at a larger diameter, and the robotic transport (162) is further so adapted to the optical probe (106) as to move the optical probe inside the redrilled hole to remeasure the drilled hole at different depths with the same optical probe.

Also in the example of FIG. 1, the end effector has mounted upon it a cleaning apparatus (174) that includes a compressed air nozzle (178) and an industrial wire or non-wire brush (176) both of which are adapted to the end effector so as to facilitate cleaning both a drilled hole before scanning the hole with the probe and also to clean the probe itself. Alternatively, the end effector may implement a vacuum to clean the drilled hole. As with the drilling apparatus, the cleaning apparatus may reside on the same robotic transport or on an entirely different robotic transport and may be rotated or translated into position with respect to a hole.

In the example of FIG. 1, the surface (172) with drilled holes is illustrated as a wing of an aircraft with a callout (166) illustrating a section (170) of the surface with the drilled holes (180). But readers of skill in the art will understand that apparatus for optical measurement of drilled holes according to embodiments of the present invention are adapted to optical measurement of drilled holes on many surfaces, automotive, aerospace vehicles, and so on. In addition, the drilled holes (180) in the example of FIG. 1 are illustrated as countersunk with a single diameter in a single material, but readers will recognize that measurement of drilled holes according to embodiments of the present invention is carried out among through-holes, holes with variable diameters, holes through a variety of construction materials, aluminum, steel, titanium, composites, and so on.

The apparatus of FIG. 1 can be used to produce a 3D reconstruction of a drilled hole for viewing by an operator. The 3D reconstruction is generated by registering by the controller (156) in memory (168) all of the cross-section measurement data into a three-dimensional point cloud or mesh. The cross-section measurement data in this sense is composed of data read from sensor illumination of reflected rings of light.

The relative position of the cross-sections is determined by the speed of the robotic transport's movement of the probe within a hole as set when the controller and the transport were programmed—and the frame rate of the optical sensor (112). The three-dimensional data can be rendered on a display such as a graphical user interface.

Because some materials have optical properties that do not lend themselves well to optical measurement, an opacifying material may be blown onto the drilled hole prior to measuring it and after the drilled hole has been cleaned. An example of an opacifier is talc or silicone powder. The material has the property of reflecting the ring of light in a predictable manner and it has a small and uniform particle size. After the hole is measured, the opacifying material may be vacuumed so that the hole is free of the material.

Figure 2:
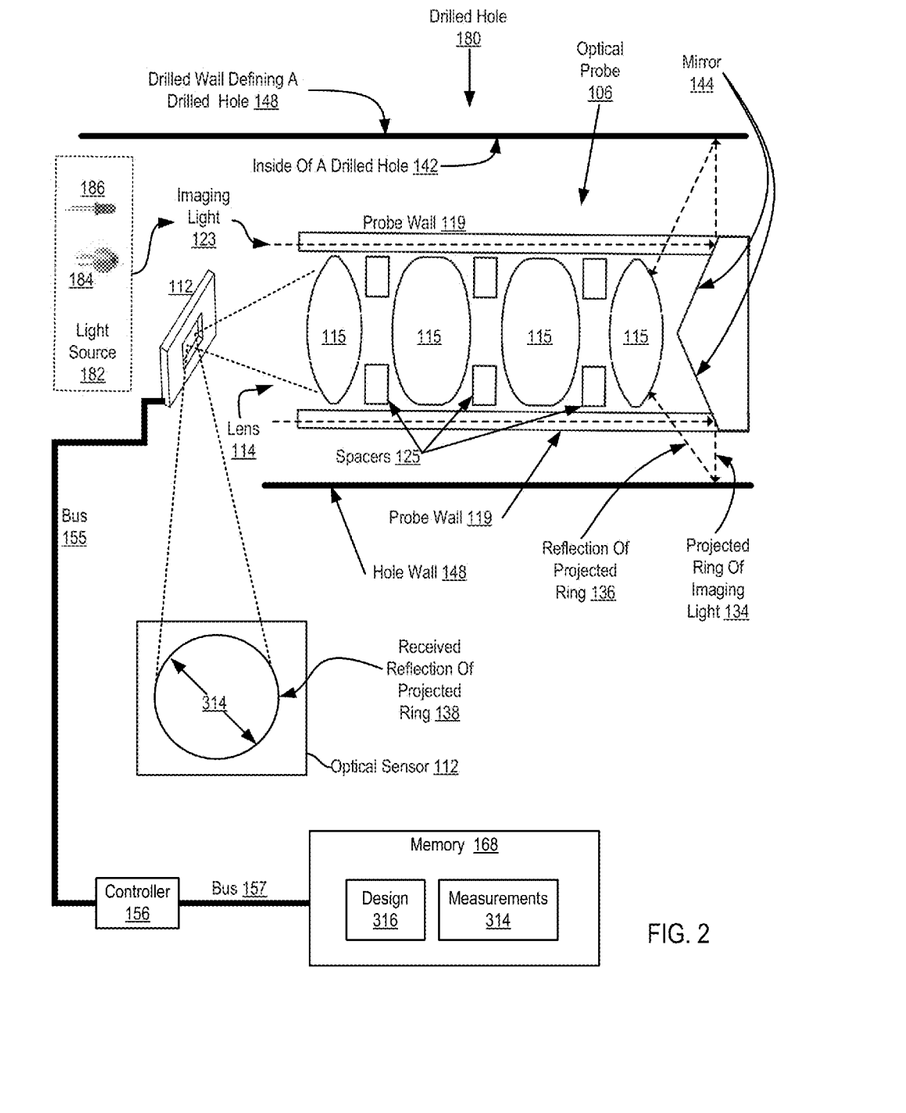
FIG. 2 sets forth a line drawing of an example optical probe for measurement of drilled holes.

For further explanation, FIG. 2 sets forth a line drawing of an example optical probe (106) for measurement of drilled hole, a component of apparatus for optical measurement of drilled holes. The drilled hole (180) in this example has a wall (148) defining the drilled hole and defining the inside (142) of the drilled hole. The optical probe (106) includes a tubular probe wall (119) and a lens (114) disposed within and supported by the probe wall (119). The lens (114) of FIG. 2 is composed of a of lens elements (115) that are separated by spacers (125). The optical probe (106) of FIG. 2 also has a light source (182) that produces imaging light (123) that is carried between the probe wall and the lens (114) to a mirror (144). The imaging light may be carried from the light source (182) to the mirror (144) by use of glass, fiber optic cables, or in other ways as will occur to those of skill in the art. In the examples of FIG. 2, imaging light (123) is conducted from a light source (182) through the tubular probe wall to the mirror that project the ring of imaging light on the inside wall of the hole. In this example, the tubular probe wall is composed of a transparent, light-conducting optical material such as, for example, optical glass or quartz crystal.

FIG. 2 illustrates two example light sources (182), a light emitting diode ('LED') (186) and a laser diode (184), both useful in optical measurement of drilled holes according to embodiments of the present invention. A laser of course emits a single wavelength of coherent light. An LED emits a small range or bandwidth of wavelengths, incoherent, but collimated in its passage through the optical probe wall. There is no limitation to any particular wavelength or number of light sources; several may be used because different wavelengths may better illuminate various materials in which holes are drilled. The illustration of LED (186) and laser diode (184) in example of FIG. 2 is for explanation and not for limitation. Many sources of light may be useful in optical measurement of drilled holes as will occur to those of skill in the art, including even white light, for example, useful for illuminating a hole for visual or video inspection.

In the example of FIG. 2, the light source (182) and the mirror (144) of the optical probe (106) projects at least one ring (134) of light on the inside (142) of the drilled hole (180) as the optical probe (106) is moved into or out of the drilled hole (180). The apparatus of FIG. 2 also includes an optical sensor (112) that receives through an optical lens (114) of the optical probe (106) reflections (136) of the projected rings (134). The optical sensor may be implemented as a charged coupled device ('CCD'), as a complementary metal oxide semiconductor ('CMOS') sensor, and in other ways as will occur to those of skill in the art.

The example of FIG. 2 also includes a controller (156), coupled to the sensor (112) through data bus (155), that determines from the received reflections (138) measurements (188) of the drilled hole (180). Measurements (314) of a drilled hole typically include drilled hole diameter, hole circularity, and inferences whether a crack may be present in a hole wall. The controller (156) may be implemented as a Harvard architecture microcontroller with a control program in memory (168), a generally programmable Von Neumann architecture microprocessor with a control program in memory (168), field programmable gate array ('FPGA'), complex programmable logic device ('CPLD'), application-specific integrated circuit ('ASIC'), a hard-wired network of asynchronous or synchronous logic, and otherwise as will occur to those of skill in the art.

The controller is coupled through a memory bus (157) to computer memory (168), which in this example is used to store the controller's measurements (314) of the drilled hole as well as design (316) measurements for comparison with the actual measurements. The controller (156) of FIG. 2 also determines by comparison of design measurements (316) and the measurements (314) of the drilled hole (180) whether the hole as drilled is within design tolerance.

The controller (156) of FIG. 2 also infers from the measurements (314) whether a crack exists in the drilled hole (180) or whether a bur exists on the top and bottom surfaces of a drilled hole. The controller (156) inspects the top and bottom surfaces for burrs and the inside surface for variations in surface finish that may indicate a crack. The controller is such embodiments is programmed to determine according to image processing algorithms the location of the light source and probe in the image, and the light source and probe are configured for an expected surface finish for the material that is being inspected. If there is a significant deviation in surface finish indicating a crack or if there are burrs, the reflected ring of light does not appear as a radially symmetric ring on the sensor, rather it will have significant local variations in its appearance. That these variations are greater than a threshold is an indicator of a surface defect such as a burr or crack. Burrs can also be identified from white light images of the entrance and exit of the hole because the edge of the hole will not appear smooth and round. The bottom-facing surface can be imaged by a probe configuration whereby a telecentric or low field of view lens images reflections off a cone mirror. In such embodiments, the imaging light is configured so that reflections (136) of projected rings of light first reflect off of the mirror (144) and then back through the lens to the sensor rather than first striking the lens itself.

The example probe (106) of FIG. 2 is provided for explanation and not for limitation. In alternative embodiment, for example, the optical probe (106) comprises a telecentric or low field of view lens, a double cone mirror, and light sources located proximal and distal to the double cone mirror. The lens images the proximal-facing aspect of the double cone mirror. In some cases, the full angle of the side of the cone mirror proximal to the lens is greater than 90 degrees to permit viewing of reflections from the cone mirror that originate at locations that are proximal to the apex of the cone mirror. A proximal white light source may provide illumination for inspecting the bottom-facing surface of the drilled hole. A distal light source directs light to a distal-facing aspect of the double cone mirror that reflects the light laterally. An additional distal light source may provide white light for inspecting the top-facing surface of the drilled hole.

Figure 3:
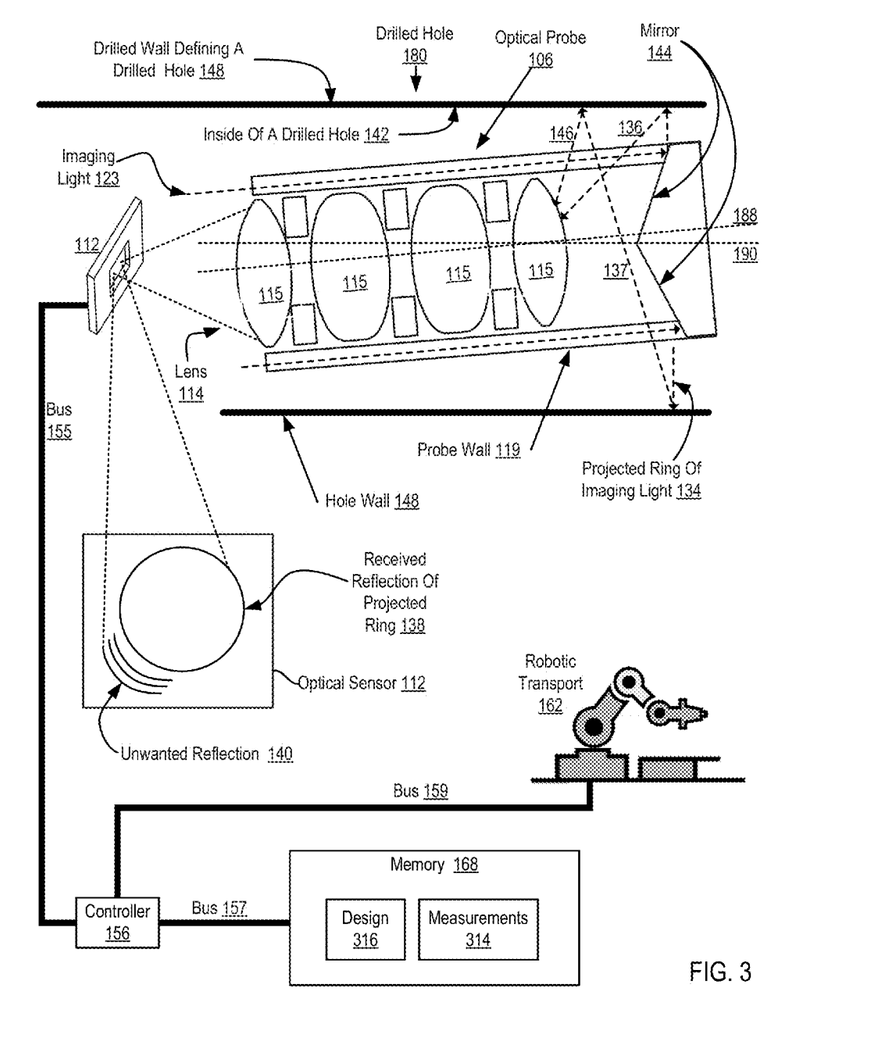
FIG. 3 sets forth sets forth a line drawing of further examples apparatus for optical measurement of drilled holes.

For further explanation of orientation or calibration of an optical probe within a drilled hole, FIG. 3 sets forth sets forth a line drawing of further example apparatus for optical measurement of drilled holes that includes an optical probe whose center axis (188) is tilted with respect to the center axis (190) of the drilled hole (180) in which the probe is moving. The robotic transport (162) in this example is adapted to receive from the controller (156) through extension bus (159) instructions to align the optical probe (106) with the center axis (188) of the optical probe parallel to the center axis (190) of the drilled hole (180) for minimal unwanted reflection (140).

The unwanted reflections (140) result from the fact of the tilt of the probe with respect to the hole, allowing at least some of the reflected light (137) to reflect through the probe and effect a second reflection (146) off the opposite wall of the hole before arriving at the lens, thereby making the appearance of a first reflection that is actually a second reflection, in effect, producing noise that indicates a wrong placement of the hole wall in the space of the hole. The controller detects the tilt by noting in its scan of optical data from the sensor (112) that in addition to the project ring itself (138) the sensor also bears illuminated pixels outside the ring, that is, illuminated pixels representing one or more unwanted reflections, unwanted reflection caused by the tilt of the probe's center axis with respect to the center axis of the hole. The controller instructs the robotic transport to tilt the probe until the unwanted reflections are minimized, thereby aligning the probe within the drilled hole. The unwanted reflections may not be completely eliminated, but minimizing them will sufficiently align the probe to effect good quality of measurement of the drilled hole.

Figure 4:
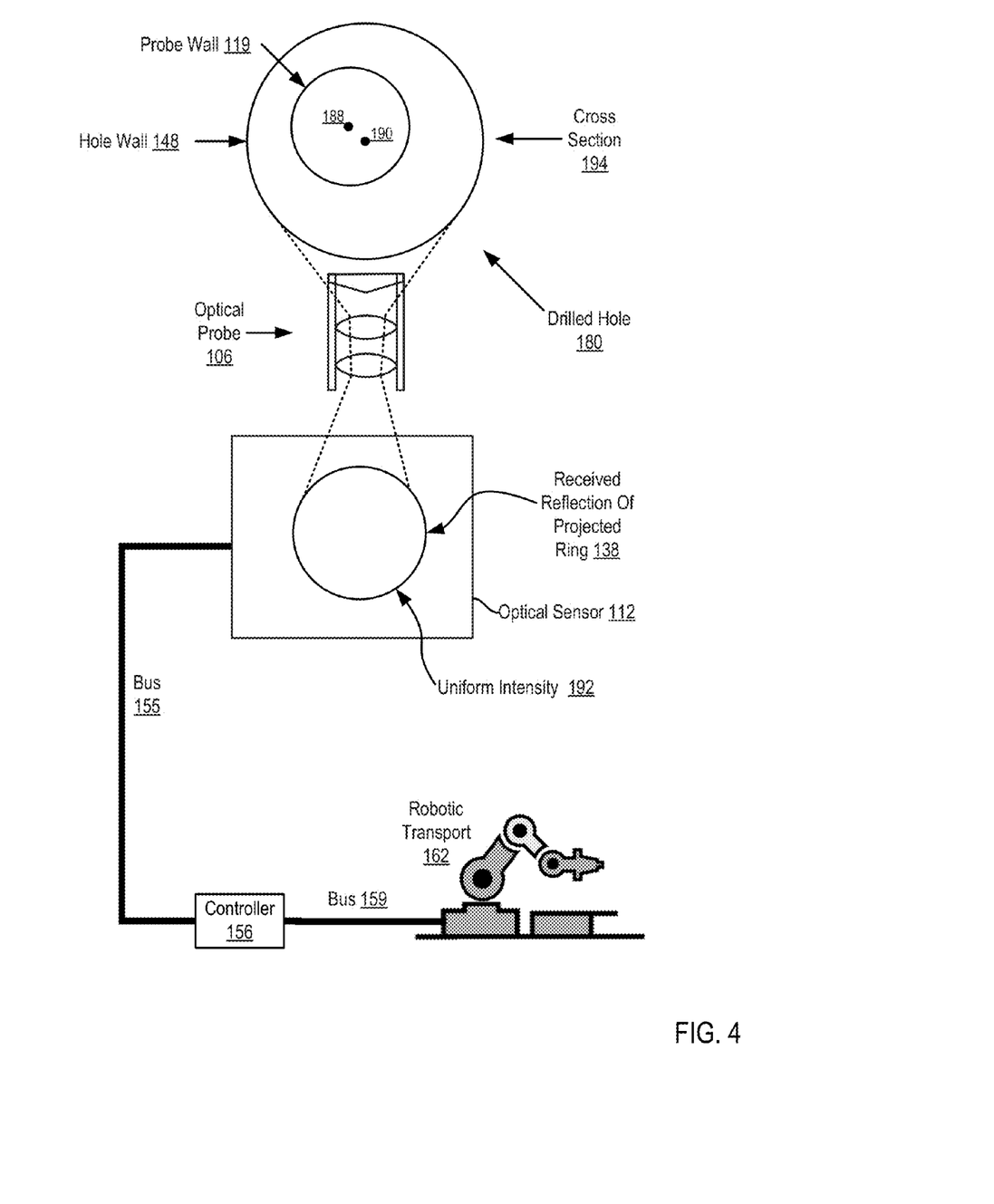
FIG. 4 sets forth sets forth a cross-sectional drawing of example apparatus for optical measurement of drilled holes.

For further explanation of orientation or calibration of an optical probe within a drilled hole, FIG. 4 sets forth sets forth a cross-sectional drawing of example apparatus for optical measurement of drilled holes that includes an optical probe (106) whose center axis (188) is parallel to the center axis (190) of a drilled hole (180) but not located exactly on the center axis (190) of the drilled hole. In fact, there is no requirement among embodiments of the present invention for the orientation of a probe to be exactly aligned on a center axis of a drilled hole in order to measure the hole. On the other hand, it is desirable for pixels that illuminate on a sensor (112) a received reflection of a projected ring (138) to be somewhat uniform in intensity to support ease of image processing by a controller (156).

In the example of FIG. 4, therefore, the robotic transport (162) is adapted to position the optical probe (106) for uniform intensity (192) of the reflections (138) received by the optical sensor (112). That is, the robotic transport (162) in this example is adapted to receive from the controller (156) through extension bus (159) instructions to position the optical probe (106) so that received reflections (138) illuminate pixels of the sensor (112) with uniform intensity. Of course "uniform intensity" is an engineering term that does not require exact uniformity. In this sense, "uniform" can be taken to mean, for example, matching a statistical mean within some predetermined variance, such as, for example, one standard deviation. Such a procedure, positioning, which is to say moving, the probe to achieve such uniformity of illumination may well move the probe toward the center of the hole, but there is still requirement of exact center alignment, and, in fact, in practice, such an exact center alignment would rarely be achieved and would be so time consuming and costly to achieve as to be of dubious value anyway. At any rate, it is not needed. What is typically the purpose in embodiments is to avoid positioning the probe so close to a hole wall as to illuminate extremely bright pixels on one side of the ring image and extremely dim pixels on the other side, thereby rendering the controller's job more difficult.

The controller (156) in this example therefore averages the intensity values as read from illuminated pixels in the received reflection (138) of a project ring of imaging light, calculates an average intensity value, and instructs the robotic transport (162) to position and reposition the probe until all the pixels in the received reflection have values within some predetermined variance from the average. The resulting positioning of the probe typically will not be exactly on the center axis of the hole, but that is of no concern among typical embodiments.

Figure 5:
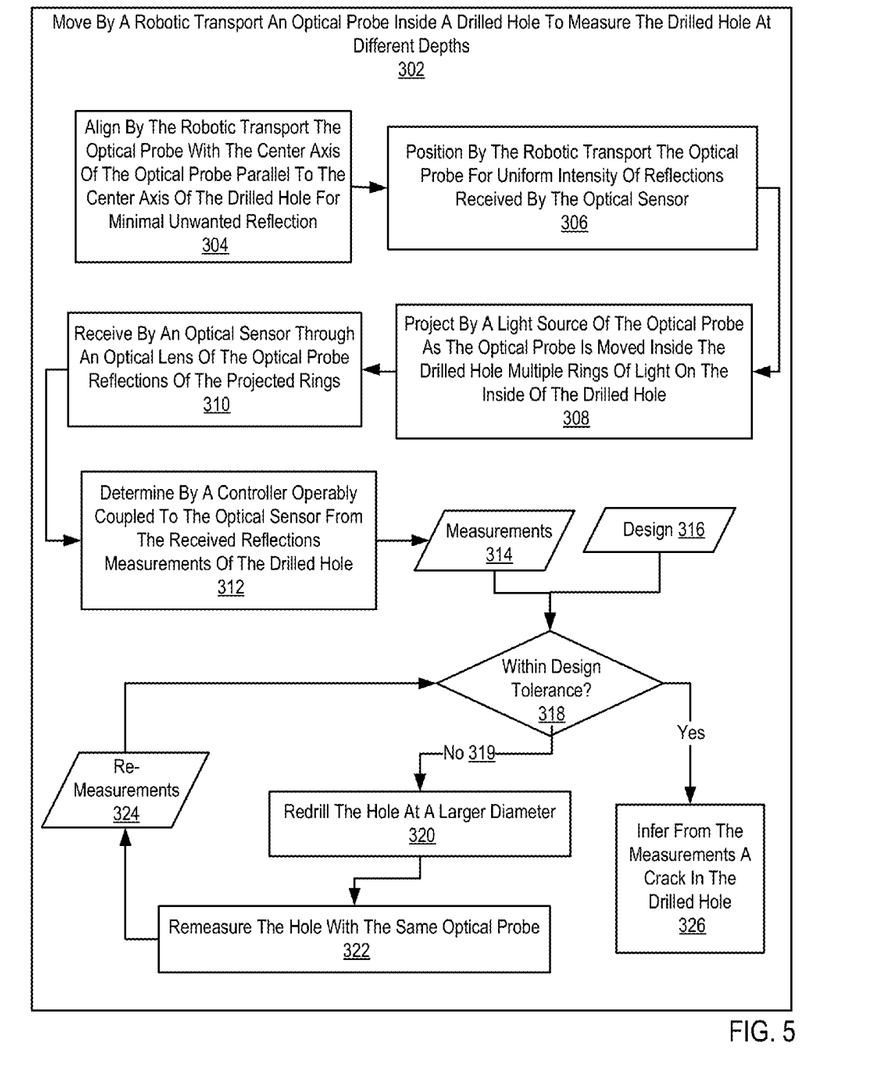
FIG. 5 sets forth a flow chart illustrating an example method of measuring a drilled hole.

For further explanation, FIG. 5 sets forth a flow chart illustrating an example method of measuring a drilled hole according to embodiments of the present invention. Although not illustrated in FIG. 5, the method of FIG. 5 is carried out by use of elements of apparatus discussed above in this specification. For clarity of reference, therefore, those elements are identified in this discussion of FIG. 5 by the reference numerals used to describe them above in the discussion of FIGS. 1-4.

The method of FIG. 5 implements moving (302) by a robotic transport (1620 an optical probe (106) inside a drilled hole (180) to measure the drilled hole (180) at one or more depths. The method of FIG. 5 includes aligning (304) by the robotic transport (162) the optical probe (106) with the center axis (188) of the optical probe (106) parallel to the center axis (190) of the drilled hole (180). This alignment is carried out by robotic transport under direction of a controller to achieve minimal unwanted reflection (140) as discussed above with reference to FIG. 3. The method of FIG. 5 also includes positioning (306) the optical probe (106) for uniform intensity of the reflections (138) received by the optical sensor (112), also carried out by the robotic transport (162) under direction of the controller as described above with reference to FIG. 4.

The method of FIG. 5 also includes projecting (308) by a light source (182) of the optical probe (106) as the optical probe (106) is moved inside the drilled hole (180) multiple rings (134) of light on the inside of the drilled hole (142); receiving (310) by an optical sensor (112) through an optical lens (114) of the optical probe (106) reflections (136) of the projected rings (134) as discussed above with reference to FIG. 2; and determining (312), by a controller (156) operably coupled to the optical sensor (112) from the received reflections (138), measurements (314) of the drilled hole also discussed above.

The method of FIG. 5 also includes determining (318) by comparison of design measurements (316) and the measurements (314) of the drilled hole whether the hole as drilled is within a design tolerance. After acquiring measurements and images of the hole, the method of FIG. 5 includes comparing the measurements against design tolerance thresholds set by for example an operator or industry standard. An operator may also be alerted if any of the measurements of the hole fall outside the tolerances. For example, an operator may set a diameter error threshold to $1/1000^{th}$ of an inch (25.4 microns). If the diameter of any of the cross-sections of the drilled hole falls outside of the nominal $+/-1/1000^{th}$ of an inch, the hole is out of tolerance and a new hole may be redrilled at a larger diameter or an operator may be notified.

The method of FIG. 5 also includes inferring (326) from the measurements (314) a crack in the drilled hole. Inferring (326) from the measurements (314) a crack in the drilled hole may be carried out by inspecting the inside surface of the drilled hole for variations in surface finish that may indicate a crack. Image processing algorithms may be used to determine the location of the light source and probe in the image and the light source and probe are configured for an expected surface finish for the material that is being inspected. If there is a significant deviation in surface finish indicating a crack, the reflected ring of light does not appear as a radially symmetric ring on the sensor, rather it will significant local variations in its appearance. When these variations are greater than a threshold it is a strong indicator of a surface defect such as a crack.

The method of FIG. 5 also includes determining (319) that the hole as drilled fails to meet a design tolerance, redrilling (320) the hole at a larger diameter, and remeasuring (322) the hole with the same optical probe. This ability to remeasure without changing probe tips is a benefit of optical measurement of drilled holes according to embodiments of the present invention. Prior art capacitive probes could not do this.

Figure 6:
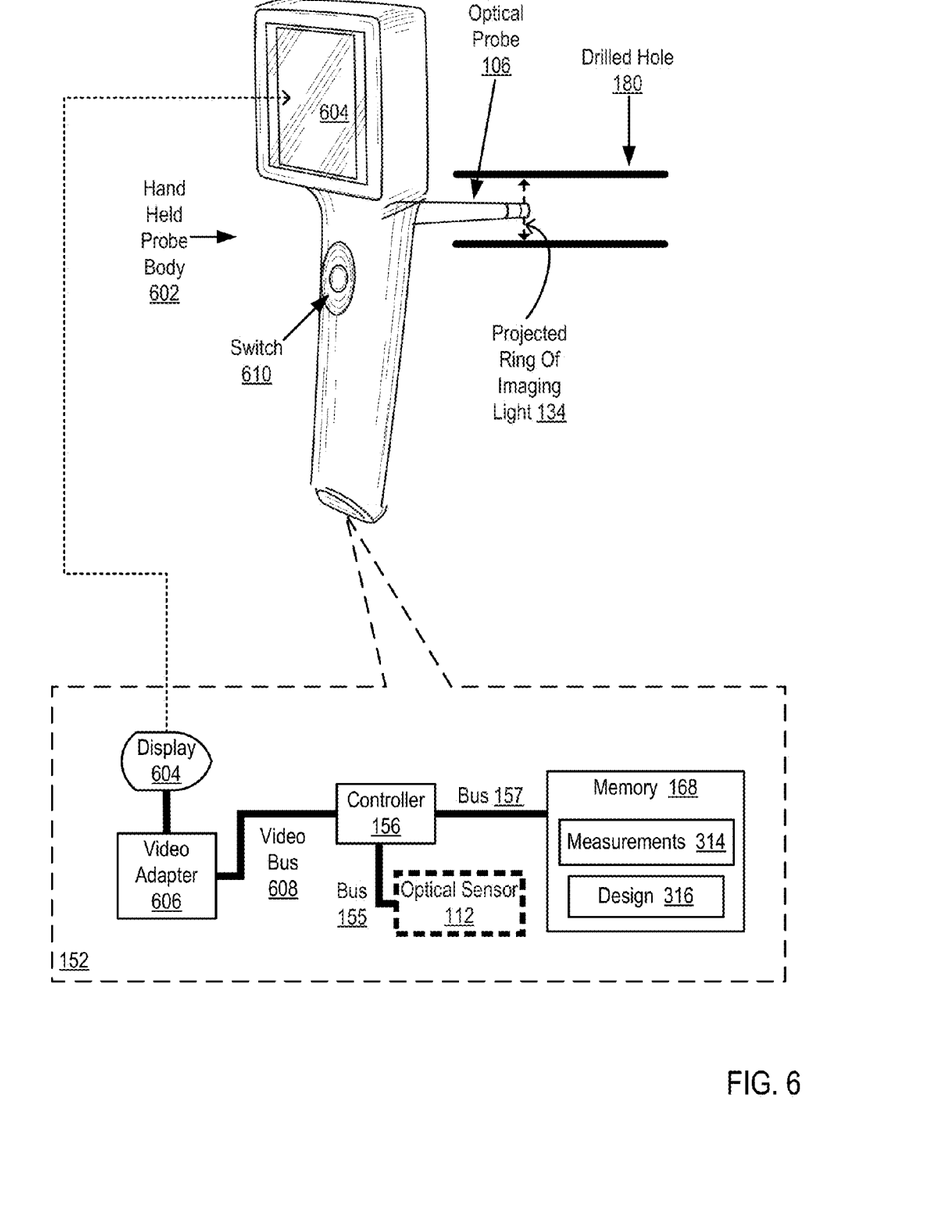
FIG. 6 sets forth a line drawing of further example apparatus for optical measurement of drilled holes.

For further explanation, FIG. 6 sets forth a line drawing of further example apparatus for optical measurement of drilled holes. The apparatus in the example of FIG. 6 includes an optical probe (106). In this example, the optical probe is mounted upon a hand held probe body (602), and the probe body also has mounted upon it a graphic display (604). An optical sensor (112) is positioned in the probe body with respect to the optical probe (106) as to sense reflected imaging light, and the sensor is operably coupled to the display (604) so as to display received reflections of rings of light from the inside of a drilled hole (180). The apparatus of FIG. 6 also includes a light source, not shown on FIG. 6 but similar to those depicted and described above with respect to FIG. 2, that projects as the optical probe is moved one or more rings of light (134) on the inside of the drilled hole (180) and a controller (156) that determines from the received reflections measurements of the drilled hole (180).

By use of the display (604), an operator by hand moves the probe inside a drilled hole, tilts the probe to minimize unwanted reflections, positions the probe for uniformity of pixel intensity, and, when the probe is aligned as desired, presses a switch (610) to instruct the controller to capture the image presently illuminated on the sensor (112) and measure the drilled hole. In the apparatus of FIG. 6 the controller (156) determines measurements of the drilled hole by comparison of design measurements and the measurements of the drilled hole whether the hole as drilled is within a design tolerance. Also in the apparatus of FIG. 6 the controller infers from the measurements whether a crack is present in the wall of the drilled hole.

The apparatus of FIG. 6 can be used to produce a 3D reconstruction of a drilled hole for viewing by an operator. The 3D reconstruction is generated by registering all of the cross-section measurement data into a three-dimensional point cloud or mesh. The relative position of the cross-sections is determined by the speed of the apparatus which was set when the apparatus is programmed and the frame rate of the optical sensor. The three-dimensional data can be rendered on the display (604).

It will be understood from the foregoing description that modifications and changes may be made in various embodiments of the present invention without departing from its true spirit. The descriptions in this specification are for purposes of illustration only and are not to be construed in a limiting sense. The scope of the present invention is limited only by the language of the following claims.

What is claimed is:

1. Apparatus comprising:
an optical probe comprising a tubular probe wall housing of optical glass and a light source that projects imaging illumination through the housing and reflects the illumination by a cone mirror as a ring of light on the inside of a drilled hole;
an optical sensor that forms, by reflections received through an optical lens of the optical probe, an image of the projected ring;
a controller operably coupled to the sensor and determining, from the image, measurements of dimensions of the drilled hole; and
a robotic transport so adapted to the optical probe as to move the optical probe inside the drilled hole to measure the drilled hole at one or more depths.

2. The apparatus of claim 1 wherein the controller determining measurements further comprises determining by comparison of design measurements and the measurements of the drilled hole whether the hole as drilled is within a design tolerance.

3. The apparatus of claim 1 wherein the controller determining measurements further comprises inferring from the measurements a crack in the drilled hole.

4. The apparatus of claim 1 wherein the controller determining measurements further comprises determining by comparison of design measurements and the measurements of the drilled hole that the hole as drilled fails to meet a design tolerance, the apparatus further comprises a drill that redrills the hole at a larger diameter, and the robotic transport is further so adapted to the optical probe as to move the optical probe inside the redrilled hole to remeasure the drilled hole at different depths with the same optical probe.

5. The apparatus of claim 1 wherein the robotic transport is adapted to align the optical probe with an axis of the optical probe that is parallel to a center axis of the drilled hole.

6. The apparatus of claim 1 wherein the robotic transport is adapted to align the optical probe with the center axis of the optical probe parallel to the center axis of the drilled hole for minimal unwanted reflection.

7. The apparatus of claim 1 wherein the robotic transport is adapted to position the optical probe for uniform intensity of the reflections received by the optical sensor.

8. A method of measuring a drilled hole, the method comprising:
moving by a robotic transport an optical probe inside a drilled hole to measure the drilled hole at one or more depths, the optical probe comprising a tubular probe wall housing of optical glass, a light source that projects imaging illumination through the housing to a cone mirror, an optical lens, and an optical sensor;
projecting by the cone mirror the imaging illumination as a ring of light on the inside of the drilled hole;
receiving by the optical sensor through the optical lens reflections of the projected ring; and
determining from the received reflections, by a controller that is operably coupled to the optical sensor, measurements of the drilled hole.

9. The method of claim 8 further comprising determining by comparison of design measurements and the measurements of the drilled hole whether the hole as drilled is within a design tolerance.

10. The method of claim 8 further comprising inferring from the measurements a crack in the drilled hole.

11. The method of claim 8 further comprising determining that the hole as drilled fails to meet a design tolerance, redrilling the hole at a larger diameter, and remeasuring the hole with the same optical probe.

12. The method of claim 8 further comprising aligning by the robotic transport the optical probe with an axis of the optical probe that is parallel to a center axis of the drilled hole.

13. The method of claim 8 further comprising aligning by the robotic transport the optical probe with the center axis of the optical probe parallel to the center axis of the drilled hole for minimal unwanted reflection.

14. The method of claim 8 further comprising positioning by the robotic transport the optical probe for uniform intensity of the reflections received by the optical sensor.

15. Apparatus for optical measurement of a drilled hole, the apparatus comprising:
   an optical probe comprising a tubular probe wall housing of optical glass and a light source that projects imaging illumination through the housing and reflects the illumination by a cone mirror as a ring of light on the inside of the drilled hole;
   a hand held probe body with the optical probe disposed upon the body;
   a graphic display operably mounted upon the probe body;
   an optical sensor positioned in the probe body with respect to the optical probe to receive reflected imaging illumination and operably coupled to the display so as to display received reflections of the ring of light from the inside of the drilled hole; and
   a controller, operably coupled to the optical sensor, that determines from the received reflected imaging illumination measurements of the drilled hole.

16. The apparatus of claim 15 wherein the controller that determines measurements further comprises the controller determines by comparison of design measurements and the measurements of the drilled hole whether the hole as drilled is within a design tolerance.

17. The apparatus of claim 15 wherein the controller that determines measurements further comprises the controller that infers from the measurements a crack in the drilled hole.

* * * * *